United States Patent [19]

Reiners et al.

[11] Patent Number: 4,665,217
[45] Date of Patent: May 12, 1987

[54] (METH)-ACRYLIC ACID ESTERS AND THEIR USE

[75] Inventors: Jürgen Reiners, Leverkusen; Jens Winkel, Cologne; Erich Klauke; Carlhans Süling, both of Odenthal; Wolfgang Podszun, Cologne, all of Fed. Rep. of Germany

[73] Assignee: Bayer Aktiengesellschaft, Leverkusen, Fed. Rep. of Germany

[21] Appl. No.: 852,600

[22] Filed: Apr. 16, 1986

[30] Foreign Application Priority Data

May 7, 1985 [DE] Fed. Rep. of Germany ....... 3516256

[51] Int. Cl.$^4$ .................... C07C 125/06; C07C 69/52
[52] U.S. Cl. .................................. 560/160; 560/221; 526/246
[58] Field of Search ................. 560/160, 221; 526/246

*Primary Examiner*—Paul R. Michl
*Assistant Examiner*—Alex H. Walker
*Attorney, Agent, or Firm*—Sprung, Horn, Kramer & Woods

[57] ABSTRACT (Meth)-acrylic acid esters of the formula

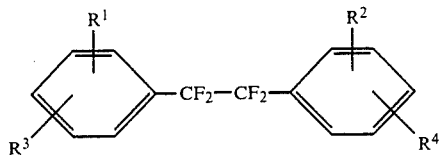

in which
$R^1$ and $R^2$ are identical or different and denote hydrogen, chlorine, fluorine or a $C_1$- to $C_4$-alkyl radical and
$R^3$ and $R^4$ are identical or different and represent the group

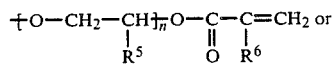

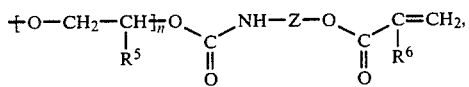

wherein
$R^5$ and $R^6$ are identical or different and denote hydrogen or methyl,
Z denotes a straight-chain or branched $C_2$- to $C_8$-alkylene chain and
n denotes values from 1 to 4. Such (meth)-acrylic acid esters can be used as dental fillers or to coat teeth.

10 Claims, No Drawings

(METH)-ACRYLIC ACID ESTERS AND THEIR USE

BACKGROUND OF THE INVENTION

The invention relates to new fluorine-containing acrylic acid and methacrylic acid esters, called (meth)-acrylic acid esters below, and their preparation. The new compounds can be employed as monomers for use in the dental field.

Fluorine-containing phenylcarbinol-acrylates, such as 1,1,1,3,3,3-hexafluoro-2-phenyl-2-acryloxy-propane, are known from *Org. Coat. Plast. Chem.*, 42, 204–207, (1980). (Meth)acrylic acid esters built up similarly, such as 1,3-bis-(2-(meth)acryloxy-1,1,1,3,3,3-hexafluoroprop-2-yl)-5-perfluoroalkyl-benzene, and their use in the dental field are described in U.S.Pat. No., 4,356,296. The carbinols are acidified by the trifluoromethyl groups and the carbinol esters prepared therefrom are distinguished by a reduced stability towards hydrolysis. Their usefulness as dental monomers is thereby limited.

The use of 1,1,5-trihydro-octafluoro-pentyl methacrylate in dental filling compositions is furthermore described in *J. Dent. Res.* 58, 1181–1186 (1979).

Monomers of this type give dental materials with inadequate mechanical properties.

SUMMARY OF THE INVENTION

New (meth)-acrylic acid esters of the formula

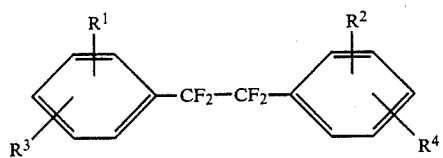
(I)

in which
R$^1$ and R$^2$ are identical or different and denote hydrogen, chlorine, fluorine or a C$_1$- to C$_4$-alkyl radical and
R$^3$ and R$^4$ are identical or different and represent the group

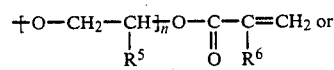

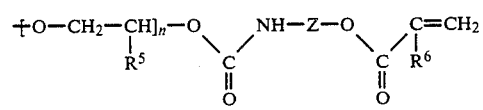

, wherein
R$^5$ and R$^6$ are identical or different and denote a hydrogen atom or a methyl group,
Z denotes a straight-chain or branched C$_2$- to C$_8$-alkylene chain and
n denotes values from 1 to 4, have been found.

The new (meth)-acrylic acid esters are colorless and of low volatility and give transparent plastics after polymerization.

They can be used particularly well in sealing agents, adhesives and dental materials, such as dental filling compositions and coating agents. The materials thus obtained are distinguished by a high resistance towards physical and chemical stress. The favorable surface properties and low water absorption of the polymers obtained with the new (meth)-acrylic acid esters are emphasized in particular.

In the context of the present invention, the substituents can in general have the following meanings.

A C$_1$- to C$_4$-alkyl radical in general denotes a straight-chain or branched hydrocarbon radical. Examples which may be mentioned are methyl, ethyl, propyl, isopropyl, butyl and iso-butyl. The methyl radical is preferred.

A C$_2$- to C$_8$-alkylene chain in general denotes a straight-chain or branched divalent hydrocarbon chain. Examples which may be mentioned are ethylene, propylene, iso-propylene, butylene, iso-butylene, pentylene, isopentylene, hexylene, iso-hexylene, heptylene, iso-heptylene, octylene and iso-octylene.

Preferred (meth)-acrylic acid esters are compounds of the formula

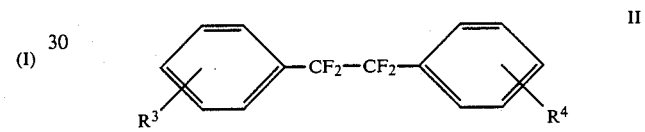
II in which
R$^3$ and R$^4$ are identical or different and represent the groups

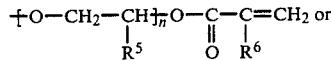

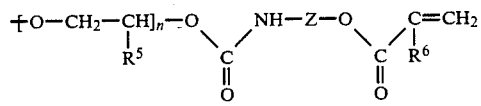

, wherein
R$^5$ and R$^6$ are identical or different and denote a hydrogen atom or a methyl group,
Z denotes a straight-chain-or branched C$_2$- to C$_8$-alkylene chain and
n denotes values from 1 to 4.

The substituents R$^3$ and R$^4$ can preferably be in the 3,3'- or 3,4'- or 4,4'-position in the 1,2-diphenyltetrafluoroethane. Compounds with R$^3$ and R$^4$ in the 4,4'-position are particularly preferred..

The following (meth)-acrylic acid esters may be mentioned as examples:

TABLE 1

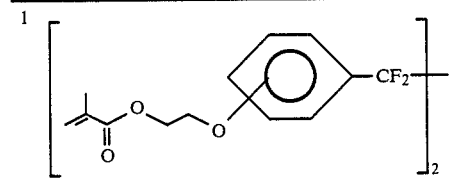

TABLE 1-continued

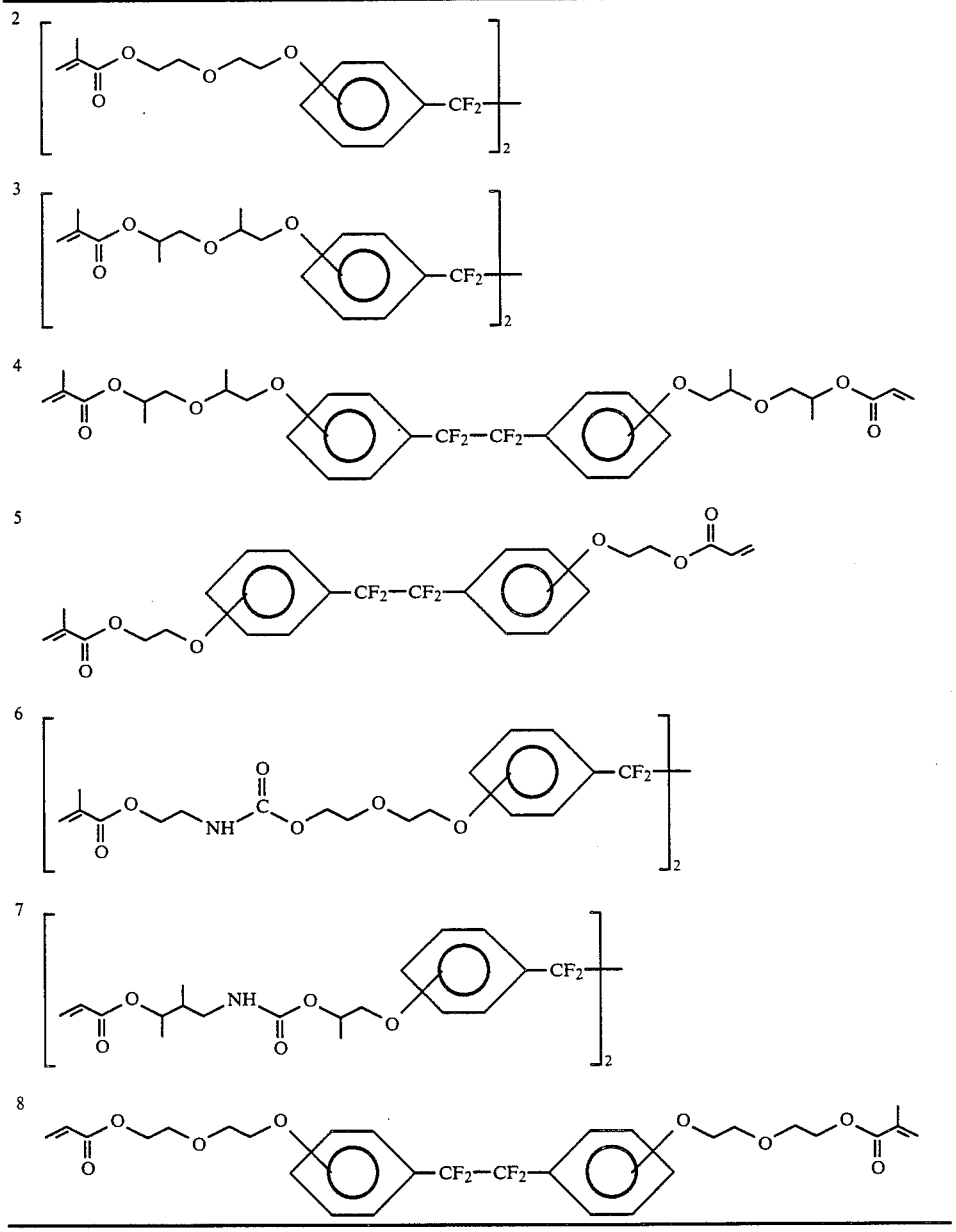

A process has also been found for the preparation of the new (meth)-acrylic acid esters. The preparation process is characterized in that a 1,2-bis-(fluorophenyl)-1,1,2,2-tetrafluoroethane of the formula

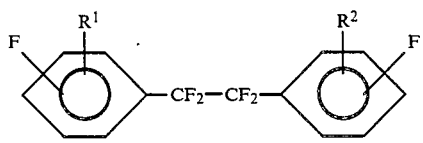
(III)

in which $R^1$ and $R^2$ are identical or different and denote hydrogen, chlorine, fluorine or a $C_1$- to $C_4$-alkyl radical, is etherified with α,ω-dihydroxy compounds of the formula $$HO-[CH_2-CHR^5-O-]_n H \qquad (IV)$$

in which n denotes values from 1 to 4 and $R^5$ denotes hydrogen or methyl, in the presence of a strong base and the reaction product is esterified with (meth)acrylic acid and/or its reactive derivatives or reacted with isocyanatoalkyl (meth)-acrylates.

DETAILED DESCRIPTION OF THE INVENTION

Compounds of the formula III are accessible, for example, in accordance with the method of L. M. Yagupolskii, V. I. Troitskaya, *Zh. Obihch. Khim.*, 35, (9), 1620 (1965) or *J. Gen. Chem. U.S.S.R.*, 35, 1616 to 1623 (1965).

α,ω-Dihydroxy compounds can be, for example, ethylene glycol, propylene glycol, diethylene glycol or triethylene glycol.

Examples of reactive derivatives of (meth)acrylic acid are the acid halides, preferably the chlorides, and esters, preferably esters of lower alcohols.

The oxyalkylation of the compounds III with the α,ω-dihydroxy compounds described above is carried out in the presence of strong bases in the temperature range from 50 to 180° C., preferably 100° to 160° C.

According to the invention, strong bases can have a $PK_B$ value of less than 3, preferably less than 2 and in particular less than 0. Examples which may be mentioned are potassium tert.-butylate and sodium and potassium isopropylate.

The products are isolated, for example, by pouring the reaction mixture onto ice-water and filtering off the precipitated crystals with suction or, in the case of liquid products, extracting the products with a waterinsoluble solvent.

The intermediates obtained by oxyalkylation have the general formula

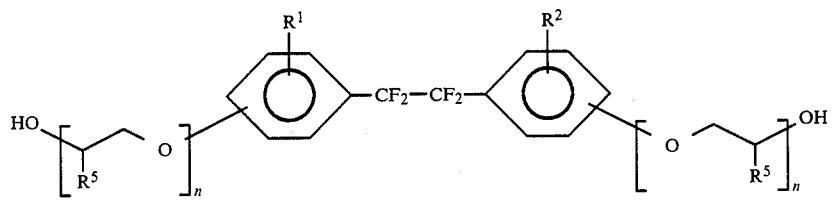

in which
R$^1$ and R$^2$ have the abovementioned meaning,
R$^5$ denotes hydrogen or a methyl group and
n denotes values from 1 to 4.

The number of oxyalkylene units added on (n) can be varied within wide limits.

n can preferably assume the values 1 or 2.

Hydroxy compounds of the formula

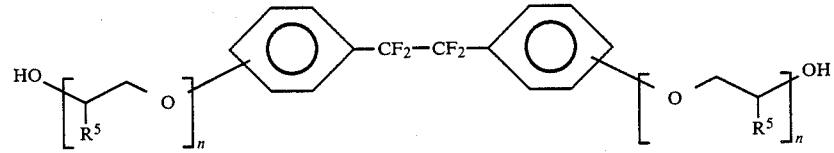

in which
n assumes values from 1 to 4 and
R$^5$ denotes a hydrogen atom or a methyl group, are particularly advantageous.

The (meth)acrylic acid esters (I) according to the invention are obtained from the hydroxy compounds of the formula (V) by esterification or by reaction with isocyanatoalkyl (meth)-acrylates.

(Meth)-acrylic acid, (meth)acrylyl chloride, (meth)-acrylic anhydride or (meth)acrylic acid esters of lower alcohols can be employed for the esterification. The esterification is preferably carried out with (meth)acrylic acid in the presence of an acid catalyst, for example, p-toluenesulphonic acid, sulphuric acid or ion exchangers in the H$^\oplus$ form, in a solvent which is water-immiscible, for example toluene, chloroform xylene and the like.

The esterification can be carried out, for example, as follows:

The hydroxy compound and an excess of (meth)acrylic acid are suspended or dissolved in a solvent, and the acid catalyst and a polymerization inhibitor are added. The water formed during the esterification is removed from the equilibrium by azeotropic distillation. The reaction is in general carried out in the temperature range from 50° C. to about 120° C. (boiling point of the azeotropic mixture about 100° C.).

Examples of suitable polymerization inhibitors are 2,6-di-tert.-butyl-4-methyl-phenol, methylene blue and hydroquinone, in an amount of 0.01.to 1% by weight. When the esterification has ended, unreacted (meth)-acrylic acid is removed by extraction with a basic aqueous solution. The inhibitor is separated off, for example, by addition of adsorbents. The reaction products according to the invention are isolated by distilling off the solvents.

Isocyanates of the formula:

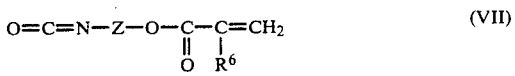

wherein
Z denotes a straight-chain or branched C$_2$- to C$_8$-alkylene chain and
R$^6$ denotes a hydrogen atom or a methyl grouo, are preferably suitable for the reaction of the hydroxy compounds according to formula V with isocyanatoalkyl (meth)-acrylates. Suitable isocyanatoalkyl(-meth)acrylates are 2-isocyanatoethyl methacrylate, 2-isocyanatopropyl methacrylate and 1,2-dimethyl-3-isocyanatopropyl acrylate.

The reaction to yield the urethane is preferably carried out with exclusion of water in an inert solvent. Examples of suitable solvents are chloroform, tetrahydrofuran, dioxane, methylene chloride, toluene and acetonitrile. Preferred solvents are chloroform, tetrahydrofuran and acetonitrile.

The reaction is in general carried out in the temperature range from 20° to 100° C., preferably 30° to 70° C. Tin-containing catalysts, such as dibutyl-tin dilaurate or tin(II) octoate, are preferably used to accelerate the reaction. Other suitable catalysts are compounds with tertiary amino groups and titanium compounds. The catalyst is in general employed in an amount of 0.01 to 2.5% by weight, preferably 0.1 to 1.5% by weight, based on the total amount of the reactants.

The reaction to give the urethane is in general carried out in the presence of 0.01 to 0.2% by weight of a polymerization inhibitor, for example 2,6-di-tert.-butyl-4-methylphenol, under normal pressure. However, it is also possible to carry out the process according to the invention under a reduced or increased pressure.

The reaction can be carried out, for example, as follows:

An isocyanatoalkyl (meth)acrylate (VII) and a hydroxy compound (V) are dissolved or suspended in the solvent, and the catalyst is added, with stirring.

After addition of the polymerization inhibitor, the reaction solution is warmed to a temperature between 20° and 100° C.

The course of the reaction with respect to time can be monitored, for example, by measuring the IR spectra. After complete reaction of the isocyanate groups, the reaction products are isolated by removing the solvent. Prior purification with the aid of adsorbents, for example, active charcoal, bleaching earth, silica gel or aluminium oxide, is possible.

For use as monomers for dental filling compositions or coating agents to coat teeth (dental lacquers) the (meth)-acrylic acid esters of the formula I according to the invention can be mixed with monomers which are known per se. for example, in order to adapt the viscosity to suit the intended use. Viscosities in the range from 60 to 10,000 mPas are preferred. This can be achieved by admixing, if appropriate, a comonomer of lower viscosity, as the reactive diluent, with the monomers according to the invention. The compounds according to the invention are employed in the mixture with comonomers in an amount of about 30 to about 90% by weight, an amount of 50 to 90% by weight being particularly preferred.

In the context of the present invention, it is also possible to employ mixtures of different (meth)-acrylic acid esters according to the invention.

It is also possible to employ monomer mixtures containing several comonomers, as the reactive diluent.

The following comonomers may be mentioned as examples: triethylene glycol dimethacrylate, tetraethylene glycol dimethacrylate, 1,12-dodecanediol dimethacrylate, 1,6-hexanediol dimethacrylate, diethylene glycol dimethacrylate and (meth)acrylic acid esters of ethoxylated or propoxylated tricyclo[5.2.1.0$^{2,6}$]decane derivatives containing hydroxyl groups (compare DE-OS (German Published Specification) 2,931,925 and 2,931,926). Comonomers which have a boiling point above 100° C. under 13 mbar are particularly preferred.

The (meth)-acrylic acid esters according to the invention, if appropriate mixed with the monomers mentioned, can be hardened by methods which are known per se (G. M. Brauer, H. Argentar, Am. Chem. Soc., Symp. Ser., 212, pages 359-371 (1983)). A system of a peroxidic compound and a reducing agent, for example based on tertiary aromatic amines, is suitable for the so-called redox polymerization, it being necessary to store the peroxide-containing and amine-containing monomer mixture separately until used, in order to prevent premature polymerization.

Examples of suitable peroxides are dibenzoyl peroxide, dilauroyl peroxide and di-chlorobenzoyl peroxide.

Examples which may be mentioned of tertiary aromatic amines are N,N-dimethyl-p-toluidine, bis-(2-hydroxyethyl)-p-toluidine, bis(2-hydroxyethyl)-3,5-dimethylaniline and the N-methyl-N(2-methylcarbamoyloxypropyl)-3,5-dimethylaniline described in German Patent Specification No. 2,759,239.

The concentration of the peroxide and of the amine are advantageously chosen such that they are 0.1 to 5% by weight, preferably 0.5 to 3% by weight, based on the monomer mixture.

The monomers according to the invention can also be brought to polymerization by irradiation with UV light or visible light (for example, in the wavelength range from 230 to 650 nm).

This is a one-component system. The advantage over redox-hardening two-component systems is that hardening of the monomer mixture is not impaired by inhomogeneities which can be caused in the redox system by inadequate mixing of the two components.

Examples of suitable initiators for the photoinitiated polymerization are benzil, benzil dimethyl ketal, benzoin monoalkyl ethers, benzophenone, p-methoxybenzophenone, fluorenone, thioxanthone, phenanthrenequinone and 2,3-bornanedione (camphorquinone), if appropriate in the presence of photoactivators with a synergistic action, such as N,N-dimethylaminoethyl methacrylate, triethanolamine and 4-N,N-dimethylaminobenzenesulphonic acid bis-allylamide. The procedure for the photopolymerization process is described, for examole, in German Patent Specification No. 3,135,115.

In addition to the initiators described above, light stabilizers and polymerization inhibitors known per se for this intended purpose can be added to the (meth)acrylic acid esters according to the invention.

The light stabilizer and the polymerization inhibitor are in general employed in an amount of 0.01 to 0.50 part by weight per 100 parts by weight of the monomer mixture. The monomer mixtures can be employed as coating agents (dental lacquers) without the addition of fillers.

When used as dental filling compositions, fillers are in general added to the resulting monomer mixtures. In order to be able to achieve a high degree of filling, monomer mixtures which have a viscosity in the range from 60 to 10,000 mPas are particularly advantageous. Inorganic fillers can preferably be admixed with the monomer mixtures containing the compounds of the formula I according to the invention. Examples which may be mentioned are rock crystal, quartzite, cristobalite, ouartz glass, highly disperse silicic acid, aluminium oxide and glass ceramics, for example glass ceramics containing lanthanum and zirconium (DE-OS (German Published Specification) 2,347,591).

The inorganic fillers are preferably pretreated with an adhesion promoter to improve bonding to the polymer matrix of the polymethacrylate. Adhesion promotion can be achieved, for example, by treatment with organosilicon compounds (Plueddemann, Progress In Organic Coatings, 11, 297 to 308 (1983)). 3-Methacryloyloxypropyl-trimethoxysilane is preferably employed.

The fillers for the dental filling compositions according to the invention in general have an average particle diameter of 0.01 to 100 μm, preferably 0.05 to 50 μm and particularly preferably 0.05 to 5 μm. It may also be advantageous to employ several fillers with different particle diameters side by side.

The content of (meth)-acrylic acid esters according to the invention in the filling compositions is in general 5 to 85% by weight, based on the filling composition.

The filler content in the dental filling compositions is in general 5 to 85% by weight, preferably 50 to 80% by weight.

To prepare the dental filling compositions, the components are processed using kneading machines which are known per se. The invention will now be described with reference to the following non-limiting examples:

PREPARATION EXAMPLES

Example 1

(A) Preparation of 1,2-bis[4-(2-hydroxyethoxy)phenyl]-1,1,2,2-tetrafluoroethane

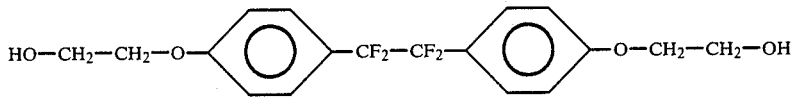

700 ml of ethylene glycol and 65 g of 1,2-bis(4-fluorophenyl)-1,1,2,2-tetrafluoroethane* are heated to 110° C. in a stirred flask. 57 g of potassium tert.-butylate are added in portions and the mixture is then stirred at 150° C. for 7 hours. The mixture is cooled, poured onto 4 liters of ice-water and mixed thoroughly with a homogenizer (Ultraturax). The crystals which have precipitated are filtered-off with suction, stirred again with 2 liters of water filtered-off with suction again, dried and recrystallized from toluene.

Yield: 39 g

Melting point: 124°–127° C.

The $^1$-H-NMR spectrum proves the structure shown above.

(B) Preparation of 1,2-bis[4-(2-hydroxyethoxyethoxy)-phenyl]-1,1,2,2-tetrafluoroethane

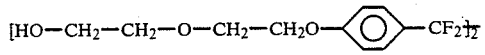

700 ml of diethylene glycol and 65 g of 1,2-bis(4-fluorophenyl)-1,1,2,2-tetrafluoroethane* are heated to 130° C. in a stirred flask and 57 g of potassium tert.-butylate are added in portions. The mixture is then heated to 150° C. and stirred at this temperature for 2 hours. The mixture is cooled, poured onto 4 liters of ice-water and mixed thoroughly with a homogenizer (Ultraturax), until crystals precipitate. The precipitate is filtered off with suction, stirred again with 3 liters of water, acidified with hydrochloric acid, filtered off with suction again, dried and recrystallized from toluene.

Yield: 70 g

Melting point: 94°–95° C.

The integrated $^1$H-NMR spectrum actuates the structure shown above.

*Chem. Abstr. Reg. No. [4100-99-6]

Example 2 (4,4'-isomer of compound 1 from Table 1)

Preparation of 1,2-bis-[4-(2-methacryloyloxy-ethoxy)-phenyl]-1,1,2,2-tetrafluoroethane 37.4 g (0.1 mole) of 1,2-bis-4-[2-hydroxy-ethoxy)-phenyl] -1,1,2,2-tetrafluoroethane, 25.8 g (0.3 mole) of methacrylic acid, 1 g of p-toluenesulphonic acid and 0.3 g of methylene blue are suspended in 100 ml of toluene.

The water is removed from the circulation by azeotropic distillation at 110° C., air having been passed through the suspension. When the separating-off of water has ended, the mixture is extracted by stirring with bleaching earth and filtered with suction and the filtrate is extracted with sodium bicarbonate solution. The organic phase is stirred with cellulose flour and filtered with suction. It is then washed neutral with sodium chloride solution. The organic phase is dried over sodium sulphate and freed from the solvent in vacuo.

Yield: 39.3 g (77%)

Melting point: 84° to 85° C.

Analysis by gas chromatography: 97%

Example 3 (4,4'-isomer of compound 2 from Table 1)

Preparation of 1,2-bis-[4-(2-methacryloyloxy-ethoxyethoxy)-phenyl]1,1,2,2-tetrafluoroethane 46.2 g (0.1 mole) of 1,2-bis-[4-(2-hydroxy-ethoxyethoxy)-phenyl]1,1,2,2-tetrafluoroethane, 25.8 g (0.3 mole) of methacrylic acid, 1 g of p-toluenesulphonic acid and 0.3 g of methylene blue are suspended in 150 ml of toluene.

The water of reaction is continuously removed from the circulation, while passing in air, over a period of 24 hours. When the reaction has ended, the mixture is extracted by stirring with bleaching earth and filtered with suction and the filtrate is extracted with sodium bicarbonate solution. The organic phase is stirred with cellulose flour and filtered with suction. It is then washed neutral with sodium chloride solution. The toluene phase is dried over sodium sulphate and freed from the solvent in vacuo.

Yield: 53.5 g (89.5%)

Melting point: 64° to 66° C.

$^1$H-NMR (CDCl$_3$) [ppm]: 1.95 (—CH$_3$, 6H), 4.5-3.7 (—CH$_2$—, 16H), 5.5–5.65 and 6.2–6.05 (=CH$_2$, 4H) and 6.75-7.5 (1,4-disubstituted phenyl radical, 8H)

Example 4 (4,4'-isomer of compound 6 from Table 1)

Preparation of 1,2-bis[4-(2-methacryloyloxyethylcarbamyloxy-ethoxyethoxy)phenyl]-1,1,2,2-tetrafluoroethane 4.62 g (10 mmol) of 1,2-bis-[4-(2-hydroxyethoxy)-phenyl]-1,1,2,2-tetrafluoroethane are dissolved in 30 ml of chloroform.

0.03 g of tin(II) octoate and 0.003 g of 2,6-di-tert. -butyl-4-methylphenol are added. 3.1 g (20 mmol) of 2-isocyanatoethyl methacrylate are slowly added dropwise at room temperature. When the addition of the isocyanate has ended, the reaction mixture is stirred at 50° C. until the IR absorption of the NCO band at 2200 cm$^{-1}$ has disappeared (a reaction time of about 5 hours). The product is isolated by removing the solvent in vacuo. The urethane is a colorless, viscous liquid., which on cooling below 10° C. becomes crystalline after several days.

Yield: 7.6 g (98.4%)

The expected structure was confirmed by the ¹H-NMR spectrum.

Example 5 ((4,4'-isomer of compound 8 from Table 1)

Preparation of
1,2-[4-(2-methacryloyloxyethoxyethoxy)-4'-2-acryloyloxy-ethoxyethoxy)]-diphenyl-1,1,2,2-tetrafluoro-ethane 46.2 (0.1 mole) of 1,2-bis-[4-(2-hydroxyethoxy-ethoxy)-phenyl]-1,1,2,2-tetrafluoroethane, 12.9 g (0.15 mole) of methacrylic acid, 10.8 g (0.15 mole) of acrylic acid, 1 g of p-toluenesulphonic acid and 0.3 g of methylene blue are suspended in 250 ml of toluene and the suspension is heated under reflux for 24 hours.

The reaction and the working up are carried out analogously to Example 3. After complete removal of the solvent, the monomer is a colourless, viscous liquid.
Yield: 51.7 g

USE EXAMPLES

Example 6

Preparation of coating solutions (a) Redox-hardening system 2.00% by weight of di-benzoyl peroxide and 0.04% by weight of 2,6-di-butyl-4-methylphenol are dissolved in a solution of the monomer mentioned in Example 5 (80 parts by weight) and triethylene glycol dimethacrylate (20 parts by weight).

2.2% by weight of N-methyl-N-(2-methylcarbamyloxypropyl)-3.5-dimethylaniline is dissolved in a second mixture which contains no peroxide but otherwise has the same composition.

A mixture of equal parts of the two solutions described above hardens in 2 to 3 minutes.

(b) Photo-curing system 0.5% by weight of 4-N,N-dimethylaminobenzenesulphonic acid bis-allylamide, 0.125% by weight of benzil dimethyl ketal, 0.2% by weight of bicyclo[2,2,1]-1,7,7-tri-methyl-heptane-2,3-dione (2,3-bornanedione) and 0.04% by weight of 2,6-di-tert.-butyl-4-methylphenol are dissolved in a monomer mixture of 80 parts by weight of the monomer from Example 5 and 20 parts by weight of triethylene glycol dimethacrylate.

On exposure to light with a dental lamp, the liquid hardens (exposure time:40 seconds).

Example 7

Example 6 was repeated using the monomer from Example 4.

The hardened coating solutions from Examples 6 and 7 are transparent and are of high hardness.

Example 8

Preparation of a redox-hardening dental composition

Amine oaste: 2.2% by weight of N-methyl-N-(2-methyl-carbamyloxyoropyl)-3,5-dimethylaniline and 0.04% by weight of the polymerization inhibitor from Example 6 are dissolved in a monomer mixture of 80 parts by weight of the compound from Example 5 according to the invention and 20 parts by weight of triethylene glycol dimethacrylate. 5 g of this solution are processed to a paste with 15 g of a commercially available glass ceramic which has an average particle diameter of 4 μm and has been silanized with 3-methacryloyloxypropyl-trimethoxysilane.

Peroxide oaste: 2.0% by weight of dibenzoyl peroxide is dissolved in a mixture of 80 parts by weight of the compound from Example 5 according to the invention and 20 parts by weight of triethylene glycol dimethacrylate. 5 g of this solution are processed to a paste with 15 g of a commercially available glass ceramic which has an average particle diameter of 4 μm and has been silanized with 3-methacryloyloxypropyl-trimethoxysilane.

A mixture of equal parts of amine paste and peroxide paste hardens within 2 to 3 minutes.

Example 9

Preparation of a photo-curing dental filling material 0.2% by weight of 2,3-bornanedione, 0.125% by weight of benzil dimethyl ketal and 0.5% by weight of 4-N,N-dimethylaminobenzenesulphonic acid bis-allylamide and 0.04% by weight of 2,6-di-tert.-butyl-4-methylphenol are dissolved in a mixture of 80 parts by weight of the monomer from Example 5 and 20 parts by weight of triethylene glycol dimethacrylate.

5 g of this solution are processed to a paste with 15 g of the filler described in Example 8 (filler content of 75%).

Hardening is carried out by exposure to light with a dental lamp. The hardening deoth is 6.1 mm at an exposure time of 40 seconds.

Example 10

Example 9 was repeated using the compound from Example 4.

Example 11

Measurement of surface tensions of the solids

Measurements of the surface tension were carried out on the hardened coating agent from Example 6. The dynamic wetting behaviour of liquids on the surfaces of the solid was determined by means of a video system. The surface tensions were calculated from the initial wetting angles of 5 test liquids. The results are summarized in Table 2.

TABLE 2

| | Measurement of the surface tensions of the solids | | | | |
|---|---|---|---|---|---|
| Monomer | Ratio of monomer to TEGDMA[A] | Total [mN/m] | Non-polar content [mN/m] | Polar content [mN/m] | Polar content [%] |
| Compound 8 | 80:20 | 37.3 | 31.3 | 6.0 | 16.1 |
| Comparison[B] | 70:30 | 42.2 | 28.7 | 13.5 | 32.0 |

[A]TEGDMA = triethylene glycol dimethacrylate
[B]Bisphenol A diglycidyl dimethacrylate (bis-GMA)/TEGDMA It will be understood that the specification and examples are illustrative but not limitative of the present invention and that other embodiments within the spirit and scope of the invention will suggest themselves to those skilled in the art.

We claim:

1. A (meth)-acrylic acid ester of the formula

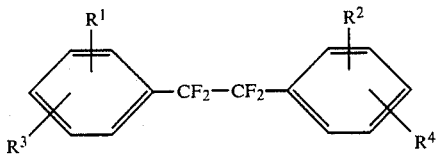

in which
R¹ and R² are identical or different and denote hydrogen, chlorine, fluorine or a C₁- to C₄-alkyl radical and
R³ and R⁴ are identical or different and represent the group

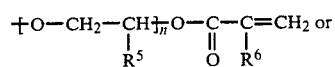

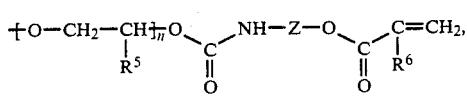

wherein
R⁵ and R⁶ are identical or different and denote a hydrogen atom or a methyl group,
Z denotes a straight-chain or branched C₂- to C₈-alkylene chain and
n denotes values from 1 to 4.

2. A (meth)-acrylic acid ester according to claim 1, of the formula

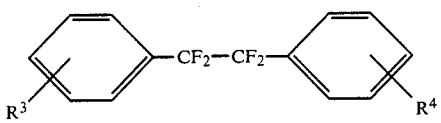

in which
R³ and R⁴ are identical or different and represent the groups

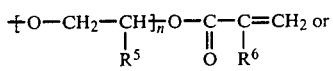

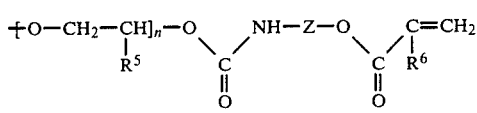

, wherein
R⁵ and R⁶ are identical or different and denote a hydrogen atom or a methyl group,
Z denotes a straight-chain or branched C₂- to C₈-alkylene chain and
n denotes values from 1 to 4.

3. A (meth)-acrylic acid ester according to claim 1, wherein the C₁-C₄-alkyl radical is selected from the group consisting of methyl, ethyl, propyl, isopropyl, butyl and iso-butyl.

4. A (meth)-acrylic acid ester according to claim 1, wherein the C₂-C₈-alkylene radical is selected from the group consisting of ethylene, propylene, iso-propylene, butylene, iso-butylene, pentylene, iso-pentylene, hexylene, isohexylene, heptylene, iso-heptylene, octylene and iso-octylene.

5. A (meth)-acrylic acid ester according to claim 1, wherein said ester is of a formula selected from the group consisting of

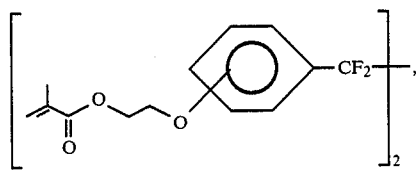

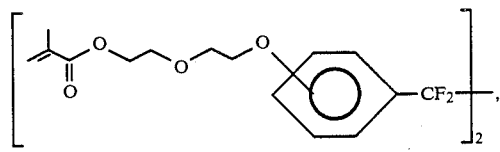

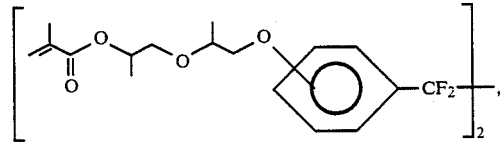

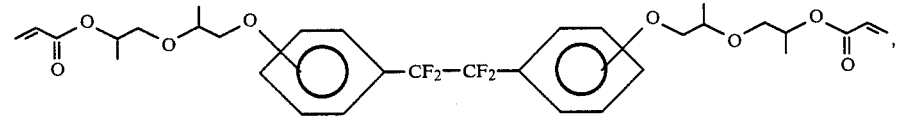

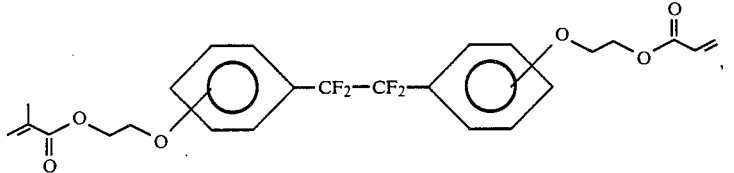

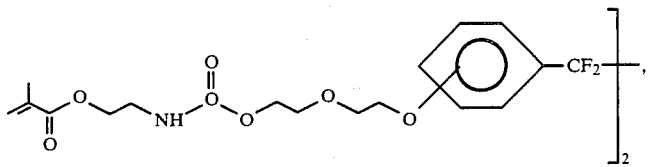

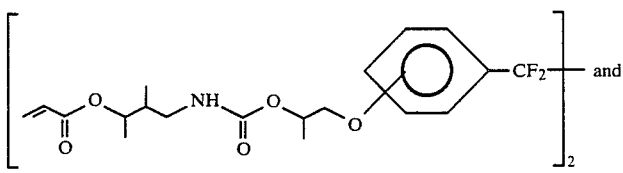

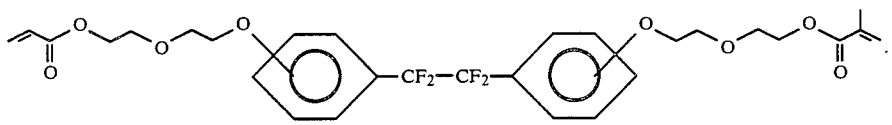

6. A process for the preparation of a (meth)-acrylic acid ester comprising etherifying a 1,2-bis-(fluorophenyl)-1,1,2,2-tetrafluoroethane of the formula

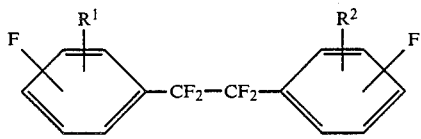

in which
R$^1$ and R$^2$ are identical or different and denote hydrogen, chlorine, fluorine or a C$_1$- to C$_4$-alkyl radical, with an α,ω-dihydroxy compound of the formula

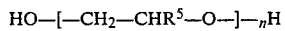

in which

R$^5$ denotes hydrogen or methyl and
n denotes values from 1 to 4, and esterifying the resultant product with (meth)-acrylic acid and/or its reactive derivatives or reacting the resultant reaction product with an iso-cyanatoalkyl(meth)-acrylate.

7. A process according to claim 6, wherein the etherification with the α,ω-dihydroxy compound is conducted in the presence of a strong base.

8. A process according to claim 6, wherein said α,ω-hydroxy compound is selected from the group consisting of ethylene glycol, propylene glycol, diethylene glycol and triethylene glycol.

9. A process according to claim 6, wherein the etherification with the α,ω-hydroxy compound is conducted at a temperature of 50° C. to 180° C.

10. A process according to claim 6, wherein the etherification with the α,ω-hydroxy compound is conducted at a temperature of 100° C. to 160° C.

* * * * *